(12) United States Patent
Selvester et al.

(10) Patent No.: US 6,947,789 B2
(45) Date of Patent: Sep. 20, 2005

(54) METHOD FOR DETECTING, SIZING AND LOCATING OLD MYOCARDIAL INFARCT

(75) Inventors: Ronald H. Selvester, Long Beach, CA (US); Peter M. Galen, McMinnville, OR (US); Joseph C. Solomon, Merrill, OR (US); Patti A. Arand, McMinnville, OR (US)

(73) Assignee: Innovise Medical, Inc., Portland, OR (US)

( * ) Notice: Subject to any disclaimer, the term of this patent is extended or adjusted under 35 U.S.C. 154(b) by 304 days.

(21) Appl. No.: 10/001,949

(22) Filed: Nov. 13, 2001

(65) Prior Publication Data

US 2002/0169383 A1 Nov. 14, 2002

Related U.S. Application Data

(60) Provisional application No. 60/248,252, filed on Nov. 13, 2000.

(51) Int. Cl.[7] .............................................. A61B 5/0452
(52) U.S. Cl. ....................................... 600/509; 600/517
(58) Field of Search ................................ 600/509, 515, 600/517, 521

(56) References Cited

U.S. PATENT DOCUMENTS

| | | | | |
|---|---|---|---|---|
| 4,998,535 | A | * | 3/1991 | Selker et al. ................ 600/509 |
| 5,501,229 | A | * | 3/1996 | Selker et al. ................ 600/508 |
| 5,792,066 | A | * | 8/1998 | Kwong ........................ 600/517 |
| 6,217,525 | B1 | * | 4/2001 | Medema et al. ............ 600/508 |
| 6,230,048 | B1 | * | 5/2001 | Selvester et al. ........... 600/523 |
| 6,507,753 | B1 | * | 1/2003 | Xue et al. .................... 600/517 |

OTHER PUBLICATIONS

Wagner et al., "Evaluation of a QRS scoring system for estimating myocardial infarct size. I. Specificity and observer agreement," 1982, Circulation, vol. 65, 342–347.*
A QRS Scoring System for Assessing Left Ventricular Function after Myocardial Infarction, Palmeri et al., The New England Journal of Medicine, Jan. 7, 1982.
Evaluation of a QRS Scoring System for Estimating Myocardial Infarct Size, Raork et al., The American Journal of Cardiology, vol. 51, Feb. 1983.
The QRS Scoring System for Estimating Myocardial Infarct Size: Clinical, Angiographic and Prognostic Correlations, Roubin et al., The American College of Cardiology, Jul. 1983.
Evaluation of a QRS Scoring System for Estimating Myocardial Infarct Size, Hindman et al., The American Journal of Cardiology, vol. 55, Jun. 1, 1985.
ECG Myocardial Infarct Size: A Gender–, Age–, Race–insensitive 12–Segment Multiple Regression Model, Selvester et al., Journal of Electrocardiology, vol. 27 Supplement, 1984.
Anatomic Validation of Electrocardiographic Estimation of the Size of Acute or Healed Myocardial Infarcts, Sevilla et al., The American Journal of Cardiology, vol. 65, Jun. 1, 1990.

* cited by examiner

Primary Examiner—Kennedy Schaetzle
(74) Attorney, Agent, or Firm—Jon M. Dickinson, P.C.; Robert D. Varitz, P.C.

(57) ABSTRACT

Algorithms for detecting, sizing and locating old myocardial infarcts by evaluating particular ECG lead data derived from selected ECG leads, where that particular data is presented hierarchically for review and confirmation, and includes selected voltage-amplitude ratios of R/Q and R/S. For a given human subject, the specific hierarchical pattern of lead data to be examined is selected on the basis of predetermined personal and demographic data, and completely in light of various, well-known, so-called confounders and excluders.

2 Claims, 2 Drawing Sheets

METHOD FOR DETECTING, SIZING AND LOCATING OLD MYOCARDIAL INFARCT

CROSS REFERENCE TO RELATED APPLICATION

This application claims priority to U.S. Provisional Patent Application Ser. No. 60/248,252 filed Nov. 13, 2000 titled "Myocardial Infarct Detecting, Sizing and Locating", and is hereby incorporated by reference.

BACKGROUND AND SUMMARY OF THE INVENTION

This invention involves conducting an analysis of input ECG and related personal data for the purpose of detecting and giving certain information about sizing and location of old myocardial infarcts (MI). In particular, the invention focuses attention on the general architecture and organization of certain algorithms which play roles in the detection, sizing and locating tasks. Featured among other things as unique in the algorithms architecture of this invention are analyses based upon selected ratios of Q, R and S voltage amplitude values which are associated with ECG data received from certain ECG leads. Two different ECG lead protocols are described herein including the usual, standard 12-lead protocol, and a known, but less widely employed 15-lead protocol.

In the setting of an interpretation and analysis system employing the algorithms of this invention, input ECG, and certain related personal data, are conventionally collected and fed into the system. This input data can generally be described as follows in relation to one preferred embodiment and method of practicing the invention, ECG data relating to a particular subject is derived from a conventional 12-lead ECG intake protocol, with data particularly focused upon which comes from leads I, II, V1, V2, V3, V4, V5 and V6.

In a modified form and implementation of the invention, data from a larger, 15-lead input protocol is used, with such data including information from each of the eight specific leads just mentioned above, and in addition, from leads V8R, V 4R and V8.

From each lead, and regardless of the specific different ways in which different pieces of conventional EGG-collection equipment may perform, what is fed into the system is lead data from these eight leads which, in the case of each lead, is based upon500-Hz sampling, 5-microvolts per least significant bit, 16-bit information, with simultaneous (from the different leads) samples spanning a duration preferably of about 10-seconds.

As will become apparent from Data Tables that form parts of the present invention disclosure, the unique algorithmic structure of the present invention examines different R/Q and R/S voltage-amplitude ratios that are associated variously with EGG data derived from leads I (ratio R/Q), AVL (ratio R/Q), AVF (ratio R/Q), V1(ratio R/S). V2(ratio R/S), V4 (ratios R/Q, R/S), V5 (ratios R/Q, R/S), V6 (ratios R/Q, R/S), V4R (ratio R/S), V8 (ratio R/Q).

In addition to EGG lead information from the leads, and of the category, mentioned above, also provided as input data for implementation of the invention is certain subject- or patient-specific data, including, for example, age, gender and race.

This "block" of data is fed into the system wherein the very first step that is performed involves the detection of so-called confounders and excluders. Confounders, a term known in the art which embraces so-called conduction abnormalities and ventricular hypertrophies, include certain conditions, such as right bundle branch block (RBBB), left anterior fascicular block (LAFB) and left and right ventricular hypertrophy (LVH and RVH). Excluders include conditions such as the presence of a pacemaker, left bundle branch block (LBBB), Wolff-Parkinson-White syndrome, and others.

The presence of confounders and/or excluders fundamentally determines how and to some extent whether data interpretation and analysis proceeds, and the algorithms proposed by the present invention are designed to be capable of dealing with certain patterns of such first-level detected conditions present in the ECG input data.

Following determination of the presence and/or absence of confounders and/or excluders, and assuming that interpretation and analysis is determined to be doable by the system which employs the algorithms of the present invention, the ECG (and mid accompanying other personal data is subjected to measurements which look at various qualities of the ECG waveforms per se, and also including a look, where appropriate, and in accordance with a feature of the present algorithms, at certain vector ECG information. Based upon these selected measurements, analysis proceeds to determine, first of all, whether or not an old MI is present, and, following that, and if such a condition is detected, to perform an analysis regarding size and location.

DETAILED DESCRIPTION, AND BEST MODE FOR CARRYING OUT, THE INVENTION

Figure 1:
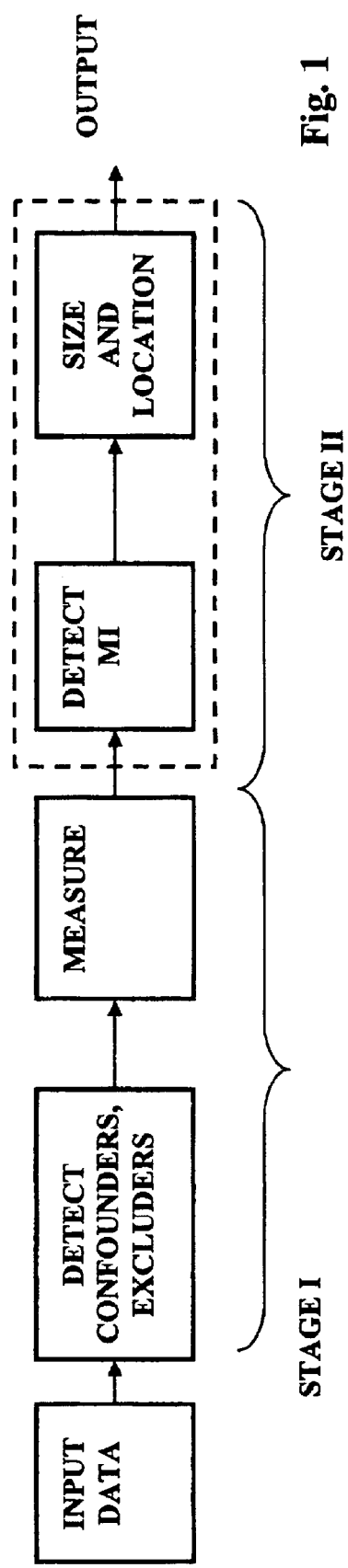
FIG. 1 in the accompanying single sheet of block-diagram sketches illustrates the overall system just generally discussed. The phrase "Stage I" is employed in this figure to characterize the operation of the blocks shown there which relate to the detection of confounders and excluders, and to the obtaining of measurements from input ECG data. The phrase "Stage II" is employed in FIG. 1 to characterize that region pictured therein which relates specifically to the algorithms constructed and employed according to the present invention. Two phases of algorithmic behavior are illustrated here, the first of which involves the process of detecting, in a "yes/no" sense, the presence or absence of an old MI condition. The second phase involves interpretation to give an indication of size and location of such a condition if one is found to be present.
Figure 2:
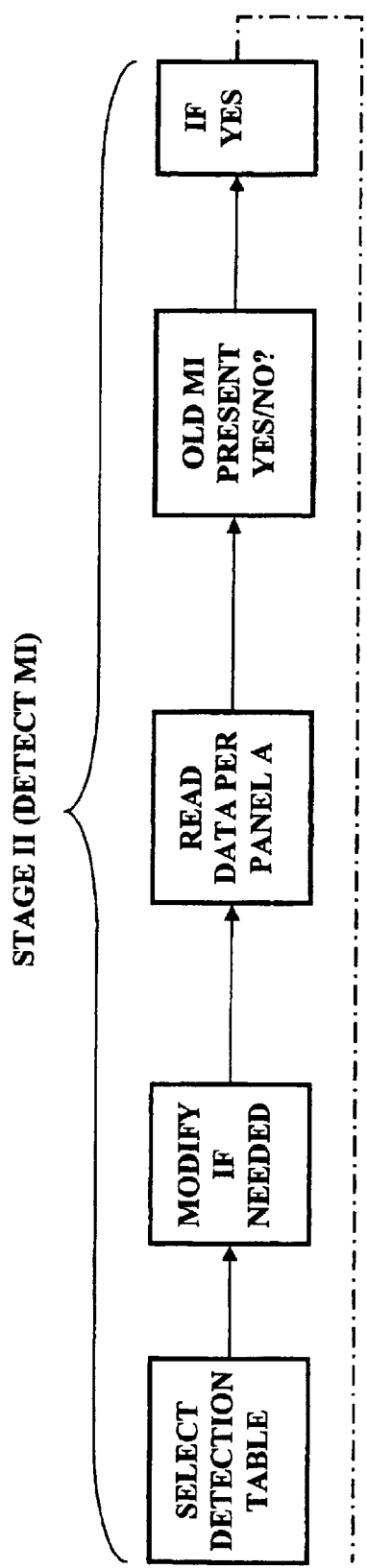
FIGS. 2 and 3 in the sketches collectively further detail the "Stage II" portion of FIG. 1, with FIG. 2 further detailing the algorithmic approach proposed herein for the detection of old MI, and with FIG. 3 further detailing the algorithmic approach employed for the interpretation of size and location of any detected old MI.
Figure 3:
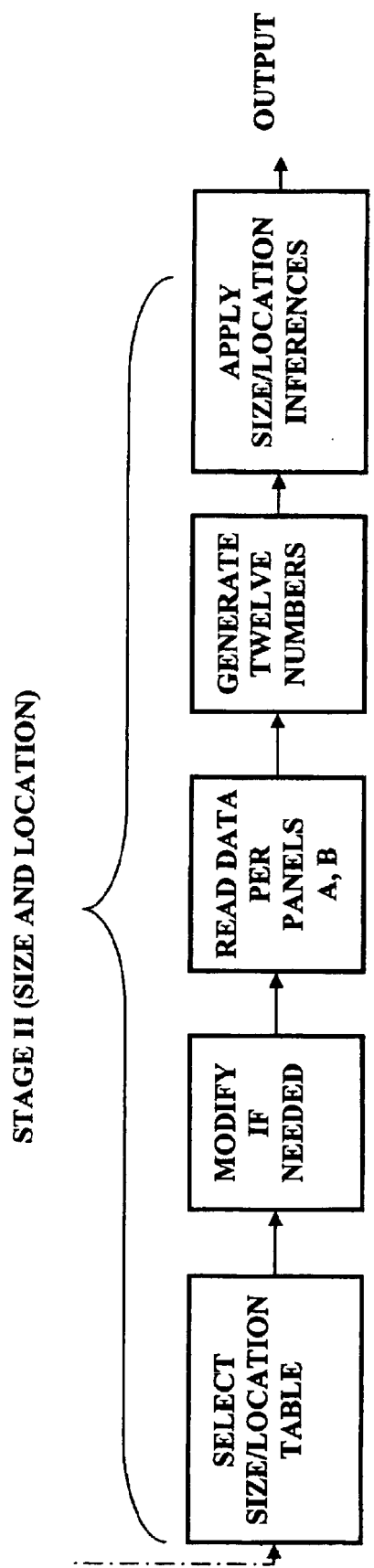

The enclosed ten Data Tables (Data Tables I–X, inclusive) generally illustrate the architectures of the algorithms of the present invention, and how the input data is handled by these algorithms to effect MI detection, sizing and location.

Table I generally relates to a situation involving ECG data received from a subject who does not have any confounding or excluding condition. Table II can be read as being an augmentation to Table I which is relevant to such a subject and under circumstances where a 15-lead input ECG protocol is employed. Table III is similar to Table I, except that it specifically relates to a subject with a right bundle branch block (RBBB) confounding condition. Table IV is also similar to Table I, except that it relates to another type of confounding condition, and namely, a left anterior fascicular block (LAFB) condition. Table V is also similar to Table I, except that here this table relates to the confounding condition known as left ventricular hypertrophy (LVH). Tables VI–IX, inclusive, simply show different ways of representing various elements found in Tables I–V, inclusive. Table X generally describes algorithmic utilization of data in various ones of the tables previously mentioned for the purpose of applying inferences to make assessments regarding MI sizing and locating. Inferences which are relevant to this determination are discussed in U.S. Pat. No. 6,230,048 issued May 8, 2001 entitled "Pictorial-Display Electrocardiographic Interpretation System and Method", and the entire content of that patent is hereby incorporated herein by reference for the purpose of elaborating the utilization of inferences.

Describing a typical interpretation event utilizing the algorithms of the present invention, with input ECG and personal information fed into the system, and after the presence of any confounders or excluders has been made, and assuming that interpretation is to go forward, what next occurs is the selection of an appropriate MI "detection" table based upon what has been found in the preliminary-analysis (look) at the input data. If that preliminary look describes a patient who has neither a confounding nor an excluding condition, then, a table very much like that presented in Data Table I is selected for the purpose of detection, and modifications are made in parameters seen in PANEL A in this Table in accordance with specific information about the subject involved, as such is set forth in the comments that appear in text below the table. For example, certain modifications will be made in the PANEL A measurement criteria depending upon whether the subject is male or female, Caucasian, black, etc. and also based upon age. The criteria specifically presented in PANEL A is based upon one particular kind of subject, (Caucasian male age 50, for example,) so modifications will need to be made for most subjects. The algorithm involved here thus performs these virtual modifications of criteria, and then reads the measurement data which has been developed previously for the purpose of making a determination about whether there is or is not an old MI present.

In evaluating ECG data from each of the several leads identified in Table I, the vertical list of values, associations and ratios to be assessed in relation to that lead (seen as a list in the table) the form of a list which includes one or more of (a) nonhierarchical, (b) hierarchical, and (c) a blend of these two, categories of constituents. The algorithm essentially "goes down" that list to find "confirmations" of categories of constituents, assigning a predetermined weighted assessment value to each confirmed constituent up to but not beyond the Lead Maximum Point count (column 3 in PANEL A) permitted according to the algorithm.

Those skilled in the art looking at the algorithmic listing of the per-lead elements, constituents, ratios, relationships, etc. presented in the Data Tables, along with the weighted assessment values, and the maximum permitted point counts set forth, will readily understand the logic of the hierarchies presented in the tables. The weighted assessment value assignation is done according to the two columns of numbers appearing along the right side of PANEL A in Data Table I. These assessments numbers present are employed for the purpose of declaring the presence or absence of an MI.

Such a "yes/no" declaration, if "no" ends the process and if "yes" effectively hands off the interpretation task to the second phase of Stage II algorithmic performance wherein size and location are assessed. Algorithmic assessment of size and location follows a pattern which is somewhat like the pattern followed by algorithmic detection of MI presence. What first occurs is the selection of an appropriate detection table, based upon subject-non ECG data, and upon the determined presence of confounding, etc. conditions. This table is, as was done earlier, modified where necessary in order to change specific criteria as such had been deemed necessary to tailor the application of the table to the particular subject. When this is done, then under algorithmic control, the input lead data are again read (hierarchically to obtain value-related confirmations) for the purpose now of creating a pattern of twelve different weighted score numbers relating to the twelve recognized segments of the Ideker quadrants of the heart (see the twelve blank rectangles at the lower-right corner of PANEL B in Data Table I, for example).

With these numbers developed, the same are read in accordance with a predetermined pattern of knowledge-based inferences, such as those described in the prior-filed patent application mentioned above herein, and the overall system, under algorithmic control, outputs an interpretation output signal which contains information that states, for example, that an old MI has indeed been found, and appears to be located at a particular region in the heart, with a certain size.

Thus, the algorithmic approach described herein is capable of taking into account various specialized input conditions, such as the confounding conditions mentioned, specifically takes into account certain pieces of personal data such as race, gender and age, and utilizes separate collections of specially selected criteria for the purpose of detecting, on the one hand, the presence or absence of an MI, and on the other hand, and thereafter, for determining the size and duration of a detected MI. Input data which is looked at according to the practice of the present algorithms includes not only timing and amplitude information, for example, of ECG waves, but also vector information relative to ECG-derived information. The algorithms specifically implement analyses based upon combined features of ECG waveforms, such as certain ratios between R and Q and R and S waveform constituents, for example, as a refined tool for assessing MI presence, size and location. The use of differentiated criteria for assessing, from input data, the presence or absence of old MI, and then the size and location of a detected MI, the utilization, where appropriate, of selected vector data, and the combining of ECG wave characteristics as an integral algorithmic behavior, produces an interpretation analysis of great sophistication.

While the invention has been disclosed in a particular setting, and in particular forms herein, the specific embodiments disclosed, illustrated and described herein are not to be considered in a limiting sense. Numerous variations, some of which have been discussed, are possible. Applicants regard the subject matter of their invention to include all novel and non-obvious combinations and subcombinations of the various elements, features, functions and/or properties disclosed herein. No single feature, function, element or property of the disclosed embodiments is essential. The following claims define certain combinations and subcombinations which are regarded as useful, novel and non-obvious. Other such combinations and subcombinations of features, functions, elements and/or properties may be claimed through amendment of the present claims or through presentation of new claims in this or in a related application. Such amended and/or new claims, whether they are broader, narrower or equal in scope to the originally presented claims, are also regarded as included within the subject matter of applicants' invention.

| PANEL A ECG POINTS (3% LV each) | | | | PANEL B % INFARCT IN 12 LV SEGS | | | | | | | | | | | |
|---|---|---|---|---|---|---|---|---|---|---|---|---|---|---|---|
| Lead | Criteria | Pts & crit | Lead Max Pt. | L A D Ant-sept,sup | | | | | | RCA Inf | | | LCX Post-lat | | |
| | | | | 1 | 2 | 3 | 4 | 5 | 6 | 7 | 8 | 9 | 10 | 11 | 12 |
| I Sup-api | Q>=30ms | 1 | | | | | | | | | | | 1 | | |
| | R/Q<=1 | 1 | 2 | | | | 1 | 1 | | | | | | | |
| | R<=0.2mV | 1 | | | | | 2 | 1 | | | | | | | |
| II Inf-api | Q>=40ms | 2 | 2 | | | | | | | 1 | 2 | 2 | 1 | | |
| | Q>=30ms | 1 | | | | | | | | 1 | 1 | | | | 1 |
| AVL Sup | Q>=30ms | 1 | 2 | | | | 2 | 1 | | | | | | | |
| | R/Q<=1 | 1 | | | | | 1 | 2 | | | | | | | |
| AVF Inf | Q>=50ms | 3 | | | | | | | | 3 | 2 | 2 | 1 | 1 | |
| | Q>=40ms | 2 | | | | | | | | 2 | 2 | 2 | | | |
| | Q>=30ms | 1 | 5 | | | | | | | 2 | 1 | | | | |
| | R/Q<=1 | 2 | | | | | | | | | 2 | 3 | | | 1 |
| | R/Q<=2 | 1 | | | | | | | | | 1 | 2 | | | |
| V1 Ant | Any | 1 | 2 | 1 | 2 | | | | | | | | | | |
| Post | R/S>=1 | 1 | | | | | | | | | 1 | 2 | | | |
| | R>=50ms | 2 | 4 | | | | | | | 1 | 1 | | 2 | 1 | 1 |
| | R>=40ms | 1 | | | | | | | | | 1 | | 1 | 1 | |
| | QRS<=0.3mV | 1 | | | | | | | | | | 1 | | 1 | 1 |
| V2 Ant | Any Q | 1 | | | | | | | | | | | | | |
| | R<=10ms | 1 | 1 | 2 | 1 | | | | | | | | | | |
| | R<=0.1mV | 1 | | | | | | | | | | | | | |
| Post | R/S>=1.5 | 1 | | | | | | | | | | 1 | | 1 | 1 |
| | R>=60ms | 2 | 4 | | | | | | | 1 | 1 | | 1 | 2 | 1 |
| | R>=50ms | 1 | | | | | | | | | 1 | 1 | | | |
| | QRS<=0.4mV | 1 | | | | | | | | | | | | 1 | 2 |
| V3 Ant | Any Q | 1 | | | | | | | | | | | | | |
| | R<=20ms | 1 | 1 | 2 | 1 | | | | | | | | | | |
| | R<=0.2mV | 1 | | | | | | | | | | | | | |
| | RV3<=RV1 | 1 | | | | | | | | | | | | | |
| V4 Ant-apical | Q>=20ms | 1 | | 1 | 1 | 1 | | | | | | | | | |
| | R/Q<=0.25 | 2 | | 3 | 2 | 1 | | | | | | | | | |
| | R/S<=0.25 | 2 | | | | | | | | | | | | | |
| | R/Q<=0.5 | 1 | 3 | | | | | | | | | | | | |
| | R/S<=0.5 | 1 | | 1 | 1 | 1 | | | | | | | | | |
| | R<=0.6mV | 1 | | | | | | | | | | | | | |
| V5 Apcl | Q>=30ms | 1 | | 1 | 1 | 1 | | | | | | | | | |
| | R/Q<=0.5 | 2 | | 1 | 1 | | 2 | 2 | | | | | | | |
| | R/S<=0.5 | 2 | | | | | | | | | | | | | |
| | R/Q<=1 | 1 | 3 | | | | | | | | | | | | |
| | R/S<=1 | 1 | | 1 | | | 1 | 1 | | | | | | | |
| | R<=0.6mV | 1 | | | | | | | | | | | | | |
| V6 Post-apical | Q>=30ms | 1 | | | | | 1 | 1 | | 1 | | | | | |
| | R/Q<=1 | 2 | | | | | | 1 | | 2 | | | 3 | | |
| | R/S<=1 | 2 | | | | | | | | | | | | | | |
| | R/Q<=2 | 1 | 3 | | | | | | | | | | | | |
| | R/S<=2 | 1 | | | | | | | | | 1 | | | 2 | |
| | R<=0.6mV | 1 | | | | | | | | | | | | | |
| TOTALS | Points-> | | %LVI> | | | | | | | | | | | | |

If > 1 criteria in bracket met, select 1 with most points
If > 1 criteria in bracket has same point, score only once
Age normalize amplitude criteria to age 50, increasing them by
1%/yr for ages 20-49 and decreasing them 1%/yr for >50yrs.
For Females further decrease all amplitude criteria by 20% → 20%
and decrease all duration criteria by 10%

DATA TABLE I

| Lead | Criteria | Pts ea crit | Lead Max Pt | L A D Ant-sept,sup | | | | | | | | RCA Inf | | | L C X Post-lat | | |
|---|---|---|---|---|---|---|---|---|---|---|---|---|---|---|---|---|---|
| | | | | 0 | 1 | 2 | 3 | 4 | 5 | 6 | 7 | 8 | | | | 2 | 4 |
| V8R Post | Q>=70ms | 2 | | | | | | | | | | | | | | | |
| | Q>=60ms | 1 | | | | | | | | | | | | | | 1 | 2 |
| V4R Ant | any Q | 1 | 1 | | 1 | 2 | | | | | | | | | 2 | 3 | 1 |
| Add Post | R>=36ms | 2 | | | | | | | | | | | | | 1 | 2 | |
| delete | R/S=4 | 3 | 4 | | | | | | | | | | | | 2 | 4 | 3 |
| | R/S>=2 | 2 | | | | | | | | | | | | | 1 | 3 | 2 |
| | R/S>=1 | 1 | | | | | | | | | | | | | 1 | 2 | |
| V8 Post | Q>=46ms | 2 | | | | | | | | | | | | | 3 | 3 | |
| | Q>=36ms | 1 | | | | | | | | | | | | | 2 | 1 | |
| | R/Q>=2 | 2 | | | | | | | | | | | | | 1 | 3 | 2 |
| | R/Q>=4 | 1 | | | | | | | | | | | | | | 2 | 1 |
| TOTALS | Points-> | | | | | | | | | | | | | | | | |
| | | | %LVI> | | | | | | | | | | | | | | |

PANEL A     PANEL B

DATA TABLE II

| PANEL A<br>ECG POINTS (3% LV each)<br>With RBBB | | Pts<br>ea<br>crit | Lead<br>Max<br>Pt | PANEL B<br>% INFARCT IN 12 LV SEGS | | | | | | | | | | | |
|---|---|---|---|---|---|---|---|---|---|---|---|---|---|---|---|
| Lead | Criteria | | | L A D<br>Ant-sept,-sup | | | | | | RCA<br>Inf | | | LCX<br>Post-lat | | |
| | | | | 1 | 2 | 3 | 4 | 5 | 6 | 7 | 8 | 9 | 10 | 11 | 12 |
| I Sup-api | Q>=30ms | 1 | | | | | | 1 | 1 | | | | 1 | | |
| | R/Q<=1 | 1 | 2 | | | | | 2 | 1 | | | | | | |
| | R<=0.2mV | 1 | | | | | | | | | | | | | |
| II Inf-api | Q>=40ms | 2 | 2 | | | | | | | 1 | 2 | 2 | | | 1 |
| | Q>=30ms | 1 | | | | | | | | | 1 | 1 | | | 1 |
| AVL Sup | Q>=30ms | 1 | 2 | | | | | 2 | 1 | | | | | | |
| | R/Q<=1 | 1 | | | | | | 1 | 2 | | | | | | |
| AVF Inf | Q>=50ms | 3 | | | | | | | | 3 | 2 | 2 | 1 | 1 | |
| | Q>=40ms | 2 | | | | | | | | 2 | 2 | 2 | | | |
| | Q>=30ms | 1 | 5 | | | | | | | | 2 | 1 | | | |
| | R/Q<=1 | 2 | | | | | | | | | 2 | 3 | | | 1 |
| | R/Q<=2 | 1 | | | | | | | | | 1 | 2 | | | |
| V1 Ant | Any Q | 1 | 2 | 1 | 2 | | | | | | | | | | |
| | Post R/S>=1 | 1 | | | | | | | | | | | 1 | 2 | |
| | R>=50ms | 2 | 4 | | | | | | | 1 | 1 | | 2 | 1 | 1 |
| | R>=40ms | 1 | | | | | | | | | 1 | | | 1 | 1 |
| | Q&S<=0.3mV | 1 | | | | | | | | | | 1 | | 1 | 1 |
| V2 Ant | Any Q | 1 | | | | | | | | | | | | | |
| | R<=10ms | 1 | 1 | 2 | 1 | | | | | | | | | | |
| | R<=0.1mV | 1 | | | | | | | | | | | | | |
| | Post R/S>=1.5 | 1 | | | | | | | | | | 1 | | 1 | 1 |
| | R>=60ms | 2 | 4 | | | | | | | 1 | 1 | | 1 | 2 | 1 |
| | R>=50ms | 1 | | | | | | | | | | 1 | 1 | 1 | |
| | Q&S<=0.4mV | 1 | | | | | | | | | | | | 1 | 2 |
| V3 Ant | Any Q | 1 | | | | | | | | | | | | | |
| | R<=20ms | 1 | 1 | 2 | 1 | | | | | | | | | | |
| | R<=0.2mV | 1 | | | | | | | | | | | | | |
| | RV3<=RV1 | 1 | | | | | | | | | | | | | |
| V4 Ant- | Q>=20ms | 1 | | 1 | 1 | | 1 | | | | | | | | |
| apical | R/Q<=0.25 | 2 | | 3 | 2 | | 1 | | | | | | | | |
| | R/S<=0.25 | 2 | | | | | | | | | | | | | |
| | R/Q<=0.5 | 1 | 3 | | | | | | | | | | | | |
| | R/S<=0.5 | 1 | | 1 | 1 | | 1 | | | | | | | | |
| | R<=0.6mV | 1 | | | | | | | | | | | | | |
| V5 Apicl | Q>=30ms | 1 | | 1 | 1 | | 1 | | | | | | | | |
| | R/Q<=0.5 | 2 | | 1 | 1 | | 2 | 2 | | | | | | | |
| | R/S<=0.5 | 2 | | | | | | | | | | | | | |
| | R/Q<=1 | 1 | 3 | | | | | | | | | | | | |
| | R/S<=1 | 1 | | 1 | | | 1 | 1 | | | | | | | |
| | R<=0.6mV | 1 | | | | | | | | | | | | | |
| V6 Post- | Q>=30ms | 1 | | | | | 1 | | | 1 | | | 1 | | |
| apical | R/Q<=1 | 2 | | | | | 1 | | | 2 | | | 3 | | |
| | R/S<=1 | 2 | | | | | | | | | | | | | |
| | R/Q<=2 | 1 | 3 | | | | | | | | | | | | |
| | R/S<=2 | 1 | | | | | | | | 1 | | | 2 | | |
| | R<=0.6mV | 1 | | | | | | | | | | | | | |
| TOTALS | Points-> | | | | | | | | | | | | | | |
| | | | %LVI> | | | | | | | | | | | | |

If > 1 criteria in bracket met, select 1 with most points
If > 1 criteria in bracket has same point, score only once
Age normalize amplitude criteria to age 60, increasing them by

DATA TABLE III

| PANEL A  ECG POINTS (3% LV each) ||| PANEL B  % INFARCT IN 12 LV SEGS ||||
|---|---|---|---|---|---|
| With LAFB | Pts ea crit | Lead Max Pt | L A D  Ant-sept,-sup  1 2 3 4 5 6 | RCA  Inf  7 8 9 | LCX  Post-lat  10 11 12 |
| I Sup-api Q>=30ms | 1 |   |   | 1 1 |   | 1 |
| R/Q<=1 | 1 | 2 |   | 2 1 |   |   |
| R<=0.2mV | 1 |   |   |   |   |   |
| II Inf-api Q>=40ms | 2 | 2 |   |   | 1 2 2 | 1 |
| Q>=30ms | 1 |   |   |   | 1 1 | 1 |
| AVL Sup Q>=40ms | 1 | 2 |   | 2 1 |   |   |
| R/Q<=1 | 1 |   |   | 1 2 |   |   |
| AVF Inf Q>=50ms | 3 |   |   |   | 3 2 2 | 1 1 |
| Q>=40ms | 2 |   |   |   | 2 2 2 |   |
| Q>=30ms | 1 | 5 |   |   | 2 1 |   |
| R/Q<=1 | 2 |   |   |   | 2 3 | 1 |
| R/Q<=2 | 1 |   |   |   | 1 2 |   |
| V1 Ant Any Q | 1 | 2 | 1 2 |   |   |   |
| Post R/S>=1 | 1 |   |   |   |   | 1 2 |
| R>=50ms | 2 | 4 |   |   | 1 1 | 2 1 1 |
| R>=40ms | 1 |   |   |   | 1 | 1 1 |
| Q&S<=0.3mV | 1 |   |   |   | 1 | 1 1 |
| V2 Ant Any Q | 1 |   |   |   |   |   |
| R<=10ms | 1 | 1 | 2 1 |   |   |   |
| R<=0.1mV | 1 |   |   |   |   |   |
| Post R/S>=1.5 | 1 |   |   |   |   | 1 1 |
| R>=60ms | 2 | 4 |   |   | 1 1 | 1 2 1 |
| R>=50ms | 1 |   |   |   | 1 | 1 1 |
| Q&S<=0.4mV | 1 |   |   |   |   | 1 2 |
| V3 Ant Any Q | 1 |   |   |   |   |   |
| R<=20ms | 1 | 1 | 2 1 |   |   |   |
| R<=0.2mV | 1 |   |   |   |   |   |
| RV3<=RV1 | 1 |   |   |   |   |   |
| V4 Ant- Q>=20ms | 1 |   | 1 1 1 |   |   |   |
| apical R/Q<=0.25 | 2 |   | 3 2 1 |   |   |   |
| R/S<=0.25 | 2 |   |   |   |   |   |
| R/Q<=0.5 | 1 | 3 |   |   |   |   |
| R/S<=0.5 | 1 |   | 1 1 1 |   |   |   |
| R<=0.6mV | 1 |   |   |   |   |   |
| V5 Apicl Q>=30ms | 1 |   | 1 1 1 |   |   |   |
| R/Q<=0.5 | 2 |   | 1 1 2 2 |   |   |   |
| R/S<=0.5 | 2 |   |   |   |   |   |
| R/Q<=1 | 1 | 3 |   |   |   |   |
| R/S<=1 | 1 |   | 1 1 1 |   |   |   |
| R<=0.6mV | 1 |   |   |   |   |   |
| V6 Post- Q>=30ms | 1 |   |   | 1 | 1 | 1 |
| apical R/Q<=1 | 2 |   |   | 1 | 2 | 3 |
| R/S<=1 | 2 |   |   |   |   |   |
| R/Q<=2 | 1 | 3 |   |   |   |   |
| R/S<=2 | 1 |   |   |   | 1 | 2 |
| R<=0.6mV | 1 |   |   |   |   |   |
| TOTALS Points-> |   |   |   |   |   |   |
|   |   | %LVI> |   |   |   |   |

DATA TABLE IV

| PANEL A<br>ECG POINTS (3% LV each) | | | PANEL B<br>% INFARCT IN 12 LV SEGS | | | | | |
|---|---|---|---|---|---|---|---|---|
| With LVH ± LAFB<br>Lead  Criteria | Pts ea crit | Lead Max Pt | L A D<br>Ant-sept.-sup<br>1 2 3 \| 4 5 6 | | | RCA<br>Inf<br>7 8 9 | LCX<br>Post-lat<br>10 11 12 | |
| I Sup-api Q>=30ms | 1 | | | 1 1 | | | 1 | |
| R/Q<=1 | 1 | 2 | | 2 1 | | | | |
| R<=0.2mV | 1 | | | | | | | |
| II Inf-api* Q>=50ms | 2 | 2 | | | | 1 2 2 | 1 | |
| * Q>=40ms | 1 | | | | | 1 1 | 1 | |
| AVL Sup Q>=40ms | 1 | 2 | | 2 1 | | | | |
| R/Q<=1 | 1 | | | 1 2 | | | | |
| AVF Inf* Q>=60ms | 3 | | | | | 3 2 2 | 1 1 | |
| * Q>=50ms | 2 | | | | | 2 2 2 | | |
| * Q>=40ms | 1 | 5 | | | | 2 1 | | |
| R/Q<=1 | 2 | | | | | 2 3 | 1 | |
| R/Q<=2 | 1 | | | | | 1 2 | | |
| V1 Ant * Any QR | 1 | 2 | 1 2 | | | | | |
| Post R/S>=1 | 1 | | | | | | 1 2 | |
| * R>=56ms | 2 | 4 | | | | 1 1 | 2 1 1 | |
| * R>=48ms | 1 | | | | | 1 | 1 1 | |
| Q & S<=0.3mV | 1 | | | | | 1 | 1 1 | |
| V2 Ant * Any QR | 1 | 1 | 2 1 | | | | | |
| RV2<RV1 | 1 | | | | | | | |
| Post R/S>=1.5 | 1 | | | | | 1 | 1 1 | |
| * R>=66ms | 2 | 4 | | | | 1 1 | 1 2 1 | |
| * R>=58ms | 1 | | | | | 1 | 1 1 | |
| Q & S<=0.4mV | 1 | | | | | | 1 2 | |
| V3 Ant * Any QR | 1 | | | | | | | |
| * R<=10ms | 1 | 1 | 2 1 | | | | | |
| * R<=0.1mV | 1 | | | | | | | |
| RV3<RV1 | 1 | | | | | | | |
| V4 Ant- Q>=20ms | 1 | | 1 1 | 1 | | | | |
| apical R/Q<=0.25 | 2 | | 3 2 | 1 | | | | |
| R/S<=0.25 | 2 | | | | | | | |
| R/Q<=0.5 | 1 | 3 | | | | | | |
| R/S<=0.5 | 1 | | 1 1 | 1 | | | | |
| R<=0.6mV | 1 | | | | | | | |
| V5 Apicl Q>=30ms | 1 | | 1 1 | 1 | | | | |
| R/Q<=0.5 | 2 | | 1 1 | 2 2 | | | | |
| R/S<=0.5 | 2 | | | | | | | |
| R/Q<=1 | 1 | 3 | | | | | | |
| R/S<=1 | 1 | | 1 | 1 1 | | | | |
| R<=0.6mV | 1 | | | | | | | |
| V6 Post- Q>=30ms | 1 | | | 1 | | 1 | 1 | |
| apical R/Q<=1 | 2 | | | 1 | | 2 | 3 | |
| R/S<=1 | 2 | | | | | | | |
| R/Q<=2 | 1 | 3 | | | | | | |
| R/S<=2 | 1 | | | | | 1 | 2 | |
| R<=0.6mV | 1 | | | | | | | |
| TOTALS  Points-> | | %LVI> | | | | | | |

DATA TABLE V

Detection Criterial Threshold:

| Criteria Thresholds (mV and mS) | Threshold | RBBB | LAFB | RVH | LVH | Points | Location | Notes |
|---|---|---|---|---|---|---|---|---|
| I Q Dur | 34 | | | | | 2 | A | 1 |
| I R/Q | 3 | | | | | 2 | A | |
| II Q Dur > OR | 32 | | | | 32 | 1 | I | |
| II R/Q | 4 | | | | | 1 | I | |
| aVL Q > OR | 36 | | | | 36 | 1 | A | |
| aVL Q Dur w/neg T aVL T | 32 | | | | 32 | 1 | A | |
| aVF Q Dur > OR | 34 | | | | 34 | 2 | I | 2 |
| aVF Q Dur w/neg aVF T | 24 | | | | 24 | - | | 3 |
| aVR R/Q | 1.8 | | | | | 1 | I | |
| V1 Q Dur | 0 | | | | | 1 | A | |
| V1 R/S > OR | 1.6 | X | | X | | 1 | P | |
| V1 R Dur | 50 | X | | X | | 1 | P | |
| V1 Q/S | 200 | X | | X | | 1 | P | |
| V2 Ant Q Dur | 0 | | | | QandR | 1 | A | 4 |
| V2 Pos R/S | .5 | X | | X | | 1 | P | |
| V2 Pos R Dur | 58 | X | | X | | 1 | P | |
| V3 Q Dur | 24 | | | | | 1 | A | |
| V4 Q Dur | 36 | | | | | 1 | A | |
| V4 R/Q > OR | 3 | | | | | 1 | A | |
| V4 R/S > OR | 0.3 | | | | | 1 | A | |
| V4 R Amp | 400 | | | | 600 | 1 | A | |
| V5 Q Dur | 32 | | | | | 2 | A | |
| V5 R/Q > OR | 5 | | | | | 2 | A | |
| V5 R/S > OR | 0.7 | | | | 1.5 | 1 | A | |
| V5 R Amp | 400 | | | | 500 | 1 | A | |
| V6 Q Dur | 32 | | | | | 1 | P | |
| V6 R/S | 2 | | | | 1.5 | 1 | P | |
| Points for 3 II neg Ts OR | | | | | | 2 | I | |
| Points for 2 II neg Ts | | | | | | 1 | I | |
| Points for 2 Ant neg Ts | | | | | | 1 | A | |
| Points for 1 aVL neg Ts | | | | | | 1 | A | |
| Points for V2-V6 | 600 | | | X | | 1 | P | |
| V2R dur AND | 20 | | | X | | - | - | |
| V2R+V3R dur | 40 | | | X | | 1 | A | 5 |
| Anterior Duration AND | 18 | | | | | 1 | A | 6 |
| Anterior Distance AND | 400 | | | | | - | - | |
| Max Posterior Amplitude | 50 | | | | | - | - | |
| Superior Distance AND | 300 | | | | | 1 | I | 7 |
| Max Superior Amplitude | 100 | | | | | - | - | |
| Anterior/Posterior Ratio AND | 2 | X | | X | | 1 | P | 8 |
| Max Anterior Amplitude | 500 | | | | | - | - | |

NOTES:
1. aVL Q Threshold changed based on presence on negative T in aVL AND I (Tamp <= T amp Threshold).
2. aVF Q scores 2 points if II Q >= 26mS, otherwise aVF Q scores 1 point.
3. aVF Q Threshold changed based on presence on negative T in aVF (aVF T amp <= T amp Threshold).
4. With LVH present, a Q followed by an R must be present to score points (Q only does not score).
5. One point for: [V2R <= 20mS] AND [(V2R+V3R) <= 40mS].
6. One point for: [Anterior Duration <= 18] AND [Anterior Distance <= 400]
7. One point for: [Superior Distance >= 300] AND [Max Superior Amp >= 100]
8. One point for: [Max Anterior Amp >= 500] AND [(Max Anterior Amp)/Max Posterior Amp) >= 2]
9. An X indicates the criteria is disabled if the given confounder is true.

DATA TABLE VI 60 yr old male

| Criteria thresholds (in uV and ms) | | RBBB | LAFB | RVH | LVH |
|---|---|---|---|---|---|
| IQDur ≤ | 34 | | | | |
| IRQS ≤ | -1 | | | | |
| IRAmp ≤ | -1 | | | | |
| IRQS ≤ | -1 | | | | |
| IIQDur ≤ | 1000 | | | | |
| IIQS ≤ | 32 | | | | 32 |
| aVLQS ≤ | 34 | | | | 34 |
| aVLQQualDur ≤ | 30 | | | | 30 |
| aVFRQS ≤ | -1 | | | | |
| aVFQDur ≤ | 1000 | | | | |
| aVFQDur ≤ | 1000 | | | | |
| aVFQS ≤ | 34 | | | | 34 |
| aVFQQualDur ≤ | 24 | | | | 24 |
| aVFRQS ≤ | -1 | | | | |
| aVFRQS ≤ | 1.8 | | | | |
| V1QDur ≤ | 0 | | | | |
| V1RS ≤ | 1.6 | X | X | | |
| V1RDur ≤ | 1000 | | | | |
| V1RDur ≤ | 54 | X | X | | |
| V1QS ≤ | 200 | X | X | | |
| V2AntQDur ≤ | 0 | | | | QandR |
| V2AntRDur ≤ | -1 | | | | X |
| V2AntRAmp ≤ | -1 | | | | X |
| V2PostRS ≤ | 5 | X | X | | |
| V2PostRDur ≤ | 1000 | | | | |
| V2PostRDur ≤ | 58 | X | X | | |
| V2QS ≤ | -1 | X | X | | |
| V2QDur ≤ | 1000 | | | | |
| V3RDur ≤ | -1 | | | | |
| V3RAmp ≤ | -1 | | | | |
| V3QDur ≤ | 24 | | | | |
| V3RDur ≤ | -1 | | | | |
| V3RAmp ≤ | -1 | | | | |
| V4QDur ≤ | 1000 | | | | |
| V4RQS ≤ | -1 | | | | |
| V4RS ≤ | -1 | | | | |
| V4RQS ≤ | 3 | | | | |
| V4RS ≤ | 0.3 | | | | |
| V4RAmp ≤ | 400 | | | | 600 |
| V5QDur ≤ | 34 | | | | |
| V5RQS ≤ | -1 | | | | |
| V5RS ≤ | -1 | | | | |
| V5RQS ≤ | 5 | | | | |
| V5RS ≤ | 0.7 | | | | 1.5 |
| V5RAmp ≤ | 370 | | | | 500 |
| V6QDur ≤ | 34 | | | | |
| V6RQS ≤ | -1 | | | | |
| V6RS ≤ | -1 | | | | |
| V6RQS ≤ | -1 | | | | |
| V6RS ≤ | 1.8 | | | | 1.5 |
| V6RAmp ≤ | -1 | | | | -1 |
| Ramp ≤ | -75 | | | | |
| Points for Inhomog ≤ | 1 | | | | |
| Pnts for 2 Inhmogs ≤ | 1 | | | | |
| Pnts for 2 Antihogs ≤ | 1 | | | | |
| V2RDur ≤ | 20 | | | | |
| V2RV3RVmin ≤ | 40 | | | | X |
| AnteriorDuration ≤ (Ant) | 15 | | | | |
| SuperiorDistance ≤ | 450 | | | | |

DATA TABLE VII

BEST AVAILABLE COPY

DATA TABLE VIII

| Lead | Criteria | Nominal Threshold | Confounder Adjustments RBBB | RVH | LAFB | LVH | Amp or Dur Adjustment | Notes | ECG Points 3% LV each Pts each Crit | Lead Max Points | % LV Infarct in 12 Segments LAD Ant-sept, sup 1 | 2 | 3 | 4 | 5 | 6 | RCA Inf 7 | 8 | 9 | LCX Post,lat 10 | 11 | 12 |
|---|---|---|---|---|---|---|---|---|---|---|---|---|---|---|---|---|---|---|---|---|---|---|
| Lead I Sup-apl | Q dur >= { ! R/Q <= OR R <= } | 34mS 4 0.15mV | - | - | - | - | Yes | | 1 1 1 | 2 | | | | 1 1 | 2 2 | 1 1 | | | | 1 | | |
| Lead II Inf-apl | {Q dur >= OR Q dur >= ) Q dur >= } Ramp/Qamp <= | 40mS 32mS 4 | - | - | - | 50mS 40mS 32mS | Yes Yes No | | 2 1 1 | 3 | | | | | | | 2 2 | 2 2 1 | 2 1 1 | | | |
| Lead aVL Sup | {Q dur >= OR Q dur >= OR Qdur >= xx w/ neg I&aVL T } Ramp/Qamp <= | 32mS - 32mS 1 | - | - | 40mS 36mS 32mS | 40mS 35mS 32mS | Yes No No | | 1 1 1 | 2 | | | | 1 1 1 | 2 2 2 1 | 2 | | | | | | |
| Lead aVF Inf-apl | {Q >= OR Q >= OR Q >= OR Qdur >= xx w/ neg aVF T } { Ramp/Qamp <= OR Ramp/Qamp <= 1 } | 50mS 42mS 34mS 24mS 1 2 | - | - | 40mS 36mS 32mS 24mS | 60mS 50mS 40mS 34mS 24mS | Yes Yes No No No | | 3 2 1 1 2 1 | 5 | | | | | | | 2 2 2 2 2 1 | 2 2 2 1 1 3 2 | 2 2 1 1 1 | | | |
| Prominent Initial Superior Forces Inf | [ Suplor Distance >= AND Maximum Superior Amplitude >= ] | 300 100 | - | - | - | - | - | 1 | 1 | 1 | | | | | | | 2 | 1 | | | | |
| Lead V1 Ant | Q dur >= (any Q) Q dur >= AND R dur >= (any QR) | 0mS X | - | X X | - | X 0mS | - - | 2 2 | 1 1 | 2 | | | | | | | | | 1 | | | |
| Post | Ramp/Samp >= { (Qamp AND Samp) <= OR (Qamp AND Samp) <= } | 1.3 0.15mV 0.20mV | X X X | X X X | - - - | - - - | Yes No | 3 | 2 1 | 2 | | | | | | 1 | | 1 1 | | 1 1 | 2 1 1 | 1 1 |
| Post 12L scoring | {R dur >= OR R dur >= } | 56mS 46mS | X X | X X | - - | - - | Yes Yes | 3 | 2 1 | 2 | | | | | | | | 1 1 | 2 1 1 | 2 1 1 | 1 1 | |
| Post 15L scoring | {R dur >= OR R dur >= } | 56mS 50mS | X X | X X | - - | - - | Yes No | 3 | 1 1 | | | | | | | | | 1 | 2 1 1 | 2 1 1 | 1 1 | |
| Lead V2 Ant | {Q dur >= (any Q) OR R dur <= R amp <= Q dur >= AND R dur >= (any QR) } | 0mS 10mS 0.04mV X | - - - - | X X X X | - - - - | X X X 0mS | - Yes Yes - | 2 | 1 1 1 1 | 1 | 1 1 1 1 | 1 1 1 1 | 1 1 1 1 | 1 1 1 1 | | 1 | | | | | | |
| Post | Ramp/Samp >= (Qamp AND Samp) <= | 3 0.30mV | X X | X X | - - | - - | Yes | | 1 | 2 | | | | | 1 | | | | 1 | | | |
| Post 12L scoring | {R dur >= OR R dur >= } | 64mS 56mS | X X | X X | - - | - - | Yes Yes | 3 | 2 1 | 2 | | | | | | | | | 1 | 2 1 | 2 1 | 1 1 |
| Post 15L scoring | {R dur >= OR R dur >= } | 64mS 58mS | X X | X X | - - | - - | Yes No | 3 | 1 1 | 1 | | | | | | | | | 1 | 1 1 | 1 2 | 1 1 |
| Prominent | [ Anterior/Posterior Ratio >= AND | 2 | X | X | - | - | - | 4 | 1 | | | | | | | | | | 1 | | | 1 | |

DATA TABLE IX

| | | | | | | | | | | | | |
|---|---|---|---|---|---|---|---|---|---|---|---|---|
| Anterior Forces | Maximum Anterior Amplitude >= | 500 | | | | | | | | | | |
| V2T - V6T Post | (V2 Tamp - V6 Tamp) >= | 0.60mV | | | | | | | | | 1 | |
| Lead V3 Ant | (Q dur >= OR | 34mS | | | | | | | | | | |
| | R amp <= OR | .040mV | | | Yes | | 2 | | 2 2 1 1 | | | |
| | Q dur >= OR | 26mS | | | Yes | | 2 | 2 | 2 2 1 1 | | | |
| | R amp <= OR | .070mV | | | Yes | | 1 | | 1 1 1 | | | |
| | Q dur >= ) | 24mS | | | Yes | | 1 | | 1 1 | | | |
| | | | | | No | | | | 1 1 | | | |
| Minimal Initial Anterior Forces Ant | [ Anterior Duration <= AND | 18 | | | | 6 | | | | | | |
| | Anterior Distance <= AND | 400 | | | | | | | | | | |
| | Maximum Posterior Amplitude >= ] | 50 | | | | | | | | | | |
| V2R+V3R dur Ant | [V2R<=20mS AND | 20mS | X | X | | 7 | 1 | | 1 | 1 | | |
| | (V2R dur +V3R dur) <= ] | 40mS | | | | | | | | | | |
| Lead V4 Ant-apical | Q dur >= | 26mS | | | Yes | | 1 | 3 | 1 1 1 | | | |
| | { Ramp/Qamp <= OR | 2 | | | | | 2 | | 2 1 1 | 2 2 1 1 | | |
| | Ramp/Samp <= OR | 0.25 | | | | | 2 | | 2 1 1 | 2 2 1 1 | | |
| | Ramp/Qamp <= OR | 4 | | | | | 1 | | 2 1 | 1 1 1 | | |
| | Ramp/Samp <= OR | 0.5 | | | | | 1 | | 2 | 1 1 | | |
| | R amp <= OR | 0.35mV | | | 0.6mV | | 1 | | 2 | | | |
| | R amp <= } | 0.4mV | | | 0.6mV | | 1 | | 2 | | | |
| Lead V5 Apical | Q dur >= | 32mS | | | Yes | | 1 | 3 | 1 1 1 | | | |
| | { Ramp/Qamp <= OR | 2.5 | | | | | 2 | | 1 1 1 | 2 2 1 1 | | |
| | Ramp/Samp <= OR | 0.35 | | | 0.75 | | 2 | | 1 1 | 2 2 1 1 | | |
| | Ramp/Qamp <= OR | 5 | | | | | 1 | | 1 | 1 1 1 | | |
| | Ramp/Samp <= OR | 0.7 | | | 1.5 | | 1 | | | 1 1 | | |
| | R amp <= OR | 0.45mV | | | 0.60mV | | | | | | | |
| | R amp <= } | 0.45mV | | | 0.50mV | | | | | | | |
| Lead V6 Post-Apical | Q dur >= | 32mS | | | Yes | | 1 | 3 | | 1 1 | 1 1 | |
| | { Ramp/Qamp <= OR | 1.8 | | | | | 2 | | | 1 1 | 2 2 1 1 | |
| | Ramp/Samp <= OR | 1 | | | 0.75 | | 2 | | | 1 1 | 2 2 1 1 | |
| | Ramp/Qamp <= OR | 3.6 | | | | | 1 | | | | 1 1 1 | |
| | Ramp/Samp <= OR | 2 | | | 1.5 | | 1 | | | | 2 1 | |
| | R amp <= } | 0.45mV | | | 0.60mV | | | | | | | |
| Lead V8 Post 15L scoring | R amp <= | 0.175mV | X | | Yes | 2 | 1 | 1 | | | 1 | 1 |
| Lead Gz Post 15L scoring | Q dur <= | 58mS | X | X | Yes | 2 | | | | | 1 | 1 |

RED: Sets limits on the allowable RAG adjustment range for the given criteria.
GREEN: Prominent Initial Superior Forces - only score if no Q detected in leads II or aVF.
BLUE: Prominent Anterior Forces - only score if no Posterior points in V1 or V2 detected.
V2 Tamp - V6 Tamp - only score if no Posterior points detected in V1 and V2 and Prominent Anterior Forces are not detected.
Minimal Initial Anterior Forces - only score if (V2 R amp <=, V2 R dur <=, V3 R amp <=) are not detected.
PURPLE: V2R+V3R duration - only score if (V2 R amp <=, V2 R dur <=, V3 R amp <=, Minimal Initial Anterior Forces) are not detected.

Scoring Table for Sizing and Locating

How to Read the Table:
1. A 'Yes' in the 'Amp or Dur Adjustments' column indicates the Nominal Threshold is adjusted for race, age, and gender (see adjustment instructions below).
2. Change threshold if a Confounder is detected and a new threshold value is indicated in the Confounder Column.
3. An 'X' indicates the criteria is ignored if the Confounder is True. Example: V1 R/S is not scored if RBBB is detected.
4. A '-' indicates no change in criteria if the Confounder is True.
5. The { } symbol indicates an OR function. Once a criteria in an OR function is met, score the appropriate points, then skip the subsequent tests in the OR brackets.
6. The [ ] symbol indicates the AND function. All criteria inside the AND function must be met to score points.

Adjustments for Race, Age, and Gender:
Some amplitude and duration criteria thresholds are adjusted for Race, Age and Gender. No criteria adjustments are made to ratio criteria (Ramp/Qamp or Ramp/Samp). Refer to the column labeled "Amp or Dur Adjustment" to determine whether an individual criteria should undergo amplitude or duration adjustments.

Amplitude Adjust:
- Age: Normalize to 50 years. Threshold = Nominal Threshold * (1 + (50-patient age)/100)
- Gender: Male, No adjustment;
  Female: Reduce Threshold by 20% (multiply threshold by 0.8)
- Race: Black: Increase threshold by 120%
  All others: No adjustments Duration Adjust:
- Gender: Male, No adjustment;
  Female: Reduce Threshold 10% (multiply threshold by 0.9)

Notes: (Refer to Table, Column heading "Notes"
1. Score points for "Prominent Initial Superior Forces" only when none of the following Criteria are met:
   II Q >=; aVF Q >=
2. Score one point for any Q unless LVH is present. If LVH detected, then 1 point scored for a Q followed by an R (Q or R only does not score)
3. Score 12 lead criteria for 12 lead ECG; Score 15 lead criteria for 15 lead ECG
4. Score points for "Prominent Anterior Forces" only when none of the following Criteria are met:
   V1 R/S >=; V1 R dur >=; V1 Q&S <=; V2 R/S >=; V2 Q&S <=; C2 Q dur >=; V8 R amp <=
5. Score points for "V2 Tamp - V6 Tamp >=" only when none of the following Criteria are met:
   V1 R/S >=; V1 R dur >=; V1 Q&S <=; V2 R/S >=; V2 Q&S <=; C2 Q dur >=; V8 R amp <=; Prominent Anterior Forces
6. Score points for "Minimal Initial Anterior Forces" only when none of the following Criteria are met:
   V2 Any Q; V2 R dur <=; V2 R amp <=; V3 R amp <=
7. Score points for "V2R dur + V3Rdur >=40mS" only when none of the following Criteria are met:
   V2 Any Q; V2 R dur <=; V2 R amp <=; V3 R amp <=; Minimal Initial Anterior Forces

DATA TABLES

We claim:

1. A method for detecting and characterizing, in the presence of confounders, a subject's old myocardial infarct (MI) comprising collecting that subject's ECG data from several preselected, standard ECG leads, establishing, in the presence of a history of confounding conditions and in relation to selected characteristics of that subject's personal data, such as, inter alia, sex, age, and/or race, a set of ECG-data criteria to examine, including R/Q and R/S voltage-amplitude ratio criteria, examining such established criteria set in the context of the mentioned history of confounding conditions, and from said examining, generating an output indicative of the desired detecting and characterizing of an old MI.

2. The method of claim 1, wherein the established R/Q and R/S ratio criteria are associated variously with one or more of ECG leads I, AVL, AVF, VI, V2, V 4, V5, V6, V4R and V8.

* * * * *